United States Patent [19]

Rainin

[11] 4,126,554
[45] Nov. 21, 1978

[54] SELECTIVELY MARKED THIN-LAYER CHROMATOGRAPHIC PLATE

[75] Inventor: Kenneth Rainin, Alamo, Calif.

[73] Assignee: Analtech, Inc., Newark, Del.

[21] Appl. No.: 830,321

[22] Filed: Sep. 2, 1977

[51] Int. Cl.² .............................................. B01D 15/08
[52] U.S. Cl. ................................ 210/198 C; 210/31 C; 427/202
[58] Field of Search ......................... 210/198 C, 31 C; 427/202, 203, 204

[56] References Cited

U.S. PATENT DOCUMENTS

| | | | |
|---|---|---|---|
| 3,623,602 | 11/1971 | Valente | 210/198 C |
| 3,864,263 | 2/1975 | Jethwa et al. | 210/198 C |

Primary Examiner—John Adee
Attorney, Agent, or Firm—Bielen and Peterson

[57] ABSTRACT

A thin-layer chromatographic plate for use with solvents utilizing a substrate having a supporting surface. An adsorbent layer of material is deposited on the supporting surface of the substrate. The adsorbent layer includes a surface separated from the substrate supporting surface which has markings selectively applied to indicate desired positions on the surface of the adsorbent layer.

15 Claims, 6 Drawing Figures

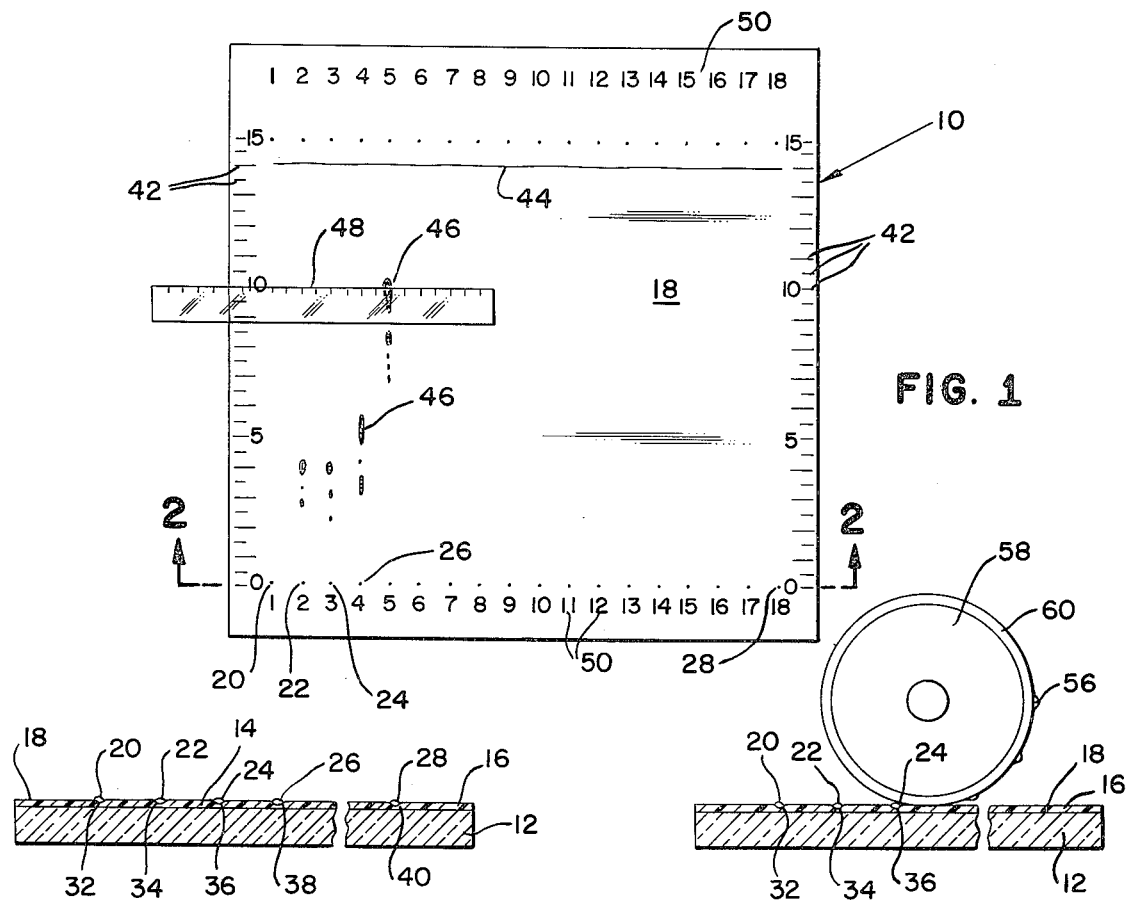
FIG. 1
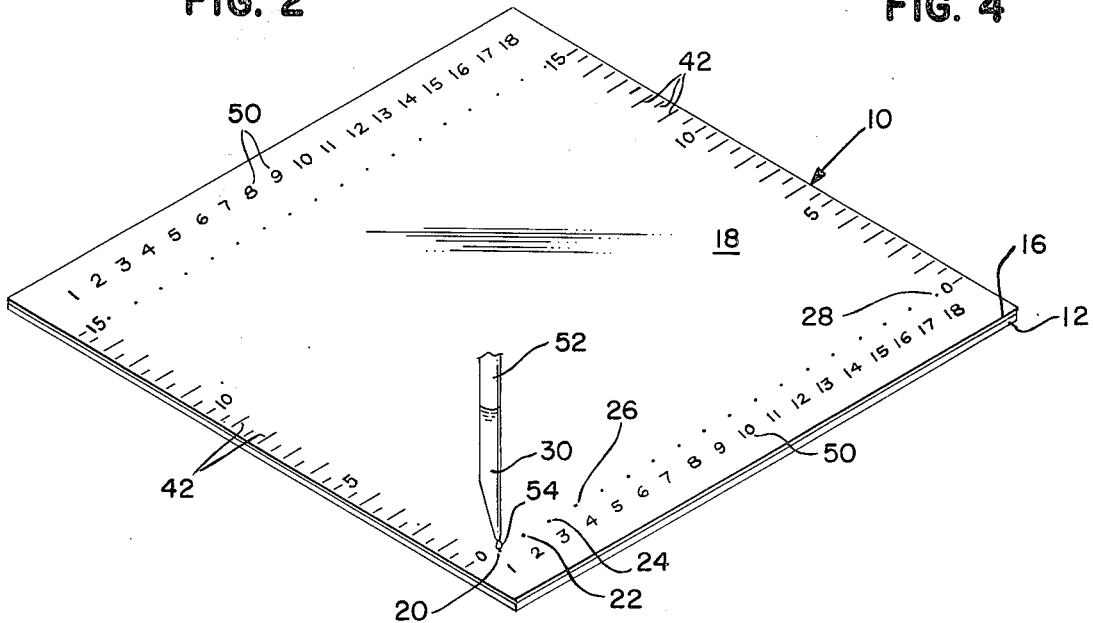
FIG. 2
FIG. 4
FIG. 3

SELECTIVELY MARKED THIN-LAYER CHROMATOGRAPHIC PLATE

BACKGROUND OF THE INVENTION

The present invention relates to a novel thin-layer chromatographic plate.

The technique known as chromatography permits the separation of chemicals to a high degree of resolution. In general, chromatographic separations depend on the solubility, adsorption, or volatility of the molecules desirous of isolation. In general, every chromatographic system consists of two phases, a moving phase and a stationary phase. The moving phase necessarily flows past the stationary phase to effect the separation.

Thin-layer chromatography is classified under the general category of adsorption chromatography. In other words, the moving phase is a liquid and the stationary phase is a solid functioning as an adsorbing surface. Formation of the adsorbing surface takes place by the deposition of adsorbent on a flat supporting surface. Prior thin-layer chromatography plates normally consist of a piece of glass having a deposit of adsorbent material, such as silica gel, alumina, kieselguhr, cellulose, and the like, in a thin layer on one side thereof. Generally, the thin-layer deposit is 0.1 to 2.0 millimeters thick. A binding agent such starch or plaster of Paris holds the adsorbent material in place. The mixture to be separated is dissolved in any suitable solvent and applied as a spot to the adsorbent surface of the plate. The solvent evaporates in a stream of warm air. The plate having the spot thereupon is then placed vertically in a chamber in contact with the solvent. The solvent ascends the adsorbent layer by capillary action to a height of about 10 to 15 centimeters above the spot. The original spot is referred to as the "origin". The top layer of solvent as it flows up the plate is known as the "solvent front". A properly selected solvent will resolve the original spot of mixture into a series of spots corresponding to a component or several components. Spots may be visualized by spraying them with suitable color producing agents such as sulphuric acid, phosphorous, and the like.

Comparison of the pattern of spots, or chromatogram, to known chromatograms completes the identification process.

The migration distance of the constituent forming the spot compared to the movement of the solvent front is critical in many identifications. Currently, spotting guides are employed such as the SJ-1010 spotting guide, distributed by Analtech, Inc., Newark, Delaware. Such guides assist in the placement of the spot and measure the migration distance of the solvent front and component spots. However, imposition of a templet or guide is awkward and often injures the relatively fragile thin-layer plate. Also, analysis samples migrate with the moving solvent leaving no trace of the origin position. Another problem arises in that thin-layer plates are often intermixed and are later unidentifiable.

No known prior thin-layer plates possess permanent indicia visible on or in the vicinity of the surface of the layer of adsorbent material.

SUMMARY OF THE INVENTION

In accordance with the present invention, a novel thin-layer chromatographic plate is provided.

The thin-layer plate of the present invention includes a substrate having a supporting surface. For example a plate of glass or plastic may be used for this purpose. An adsorbent layer of material is deposited on the supporting surface of the substrate to form an adsorbent layer presenting a surface spaced from the supporting surface of the substrate. Such an adsorbent layer may be any powdered material having a suitable binder.

The finished plate contains a mark or marks applied to the adsorbent layer and visible on its surface. Such marks may take the form of a target for the spot or origin. In addition a plurality of such targets may be aligned along a single edge of the thin-layer plate to permit multiple chromatogram development. Also, distance marks printed along the edges of the plate reveal the distance of migration of the solvent front and the spotting component. Other indicia such as serial numbers, trade names, type of adsorbent, and the like may be printed on the adsorbent layer so as not to interfere with the thin-layer chromatographic process.

Such markings may be printed directly upon the surface of the adsorbent layer utilizing marking material insoluble in the solvent or solvent component mixture. In this manner, the marking material does not interfere with chromatogram development.

Most thin-layer chromatographic plates are hardened to increase the resistance to mechanical abrasion, to increase adhesion of the adsorbent particles to the glass plate, and to bind the adsorbent particles together. Such hardened plates are delicate such that rubbing or rough handling will ruin the adsorbent layer. Printing on this surface may be accomplished by screen printing or soft photo-polymer flexing printing plates. Moreover, marking material may be transferred without physical contact between the surface of the adsorbent layer and the photo-polymer printing plate.

The thin-layer chromatographic plate of the present invention may take the form of a substrate offering support to an adsorbent layer. A margin may be placed atop the substrate to at least partially surround the adsorbent layer found on the substrate. Marking may be applied to either or both the adsorbent layer and the margin to indicate spotting origin, and distance of travel of the liquid matter.

As may be observed, a new and useful thin-layer chromatographic plate has been described, including a novel method for producing the same.

It is therefore an object of the present invention to provide a thin-layer chromatographic plate having printed indicia directly on the adsorbent layer of the plate to provide a permanent record of solvent migration, origin, and spot position, to identify components in a solvent-solute system.

It is another object of the present invention to provide a thin-layer chromatographic plate which obviates the need for spotting guides and templets which tend to mar or chip the rather delicate surface of the adsorbent layer of the plates.

It is yet another object of the present invention to provide a thin-layer chromatographic plate usable with multiple development, shaped areas, and two-dimensional thin-layer chromatographic techniques.

Another object of the present invention is to provide a thin-layer liquid chromatographic plate having written indicia directly on the adsorbent layer which is non-reactive to the chromatogram development process.

It is still another object of the present invention to provide a method for producing thin-layer chromatographic plates having selected written indicia upon the surface of the adsorbent layer to facilitate migration measurements without destruction of the adsorbent layer. The invention possesses other objects and advantages especially as concerns particular features and characteristics thereof, which will become apparent as the specification continues.

Various aspects of the present invention will evolve from the following detailed description of the preferred embodiments thereof which should be taken in conjunction with the accompanying drawings.

BRIEF DESCRIPTION OF THE DRAWINGS

FIG. 1 is a top plan view of the invention.

FIG. 2 is an enlarged, partially broken view of the invention taken along lines 2—2 of FIG. 1.

FIG. 3 is a perspective view of the invention illustrating its use during the spotting process.

FIG. 4 is a partially broken side view showing the method of application of the marks on a thin-layer chromatographic plate.

Figure 5:
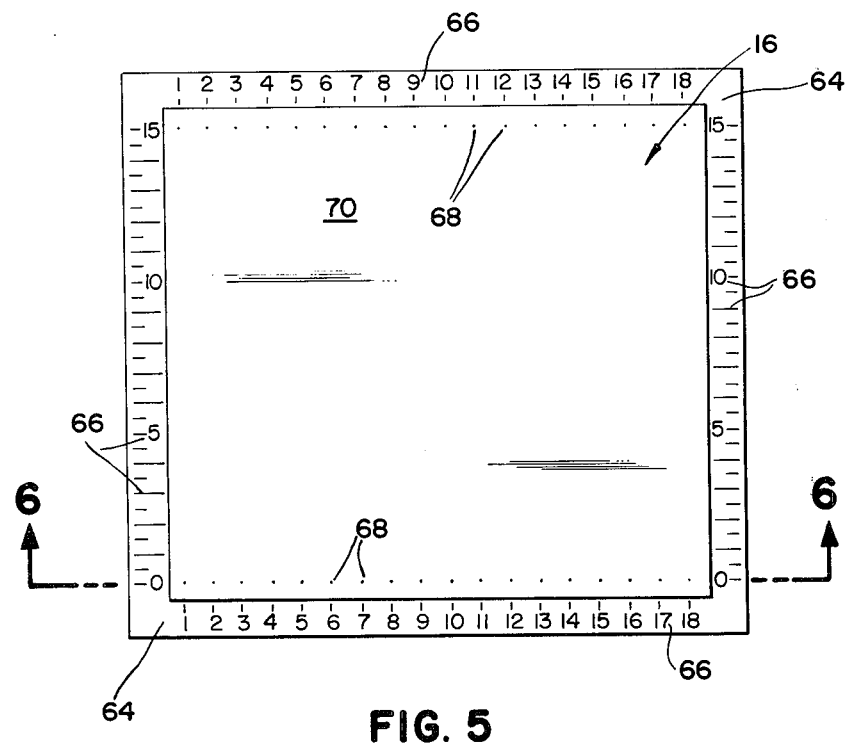
FIG. 5 is a top plan view of another embodiment of the invention.

For a better understanding of the invention, reference is made to the following detailed description.

DESCRIPTION OF THE PREFERRED EMBODIMENTS

In the accompanying drawings, the invention as a whole is denoted by reference character 10, and includes as one of its elements a substrate 12. Normally, substrate 12 provides a flat support surface 14. Substrate 12 is depicted as being constructed of glass, although plastic, aluminum foil, and other materials may be substituted depending on the nature of the separation occurring. Surface 14 is preferably smooth and uniform to provide an even surface for adsorbent layer 16, most clearly illustrated in FIG. 2.

Commonly, adsorbent layer 16 consists of a finely divided powder (passing a 200-mesh screen) of silica gel, alumina, kieselguhr, cellulose, and the like. Such a finely divided powder also contains a binder such as starch or plaster of Paris to provide a coherent structure thereto. In addition, adsorbent layer 16 may also include hardeners and adhesives to join adsorbent layer 16 to surface 14 of substrate 12. Adsorbent layer 16 may range from 0.1 to 2 millimeters in thickness. Although chromatographic plate 10 is not limited by size considerations. As such, plates 10 may range from microscopic slide sizes to quantitative thin-layer chromatography sizes on the order of 20 centimeters by 20 centimeters. Adsorbent layer 16 presents a top surface 18 spaced from surface 14 of substrate 12. Thus, substrate 12 supports adsorbent layer 16 and, in the case of glass, is impervious to most liquids.

A marking 20 may be applied to adsorbent layer 16 to indicate a certain position on surface 18 thereof. For example, marking 20 indicates or targets the exact placement of the origin 30, i.e.: the mixture of component and solvent. As depicted in FIG. 2, marks 20, 22, 24, 26, 28 also serve as origin marks for targeting the spotting of the liquid mixture 30. The thin-layer chromatographic plate 10 of the present invention shows 18 origin marks, however, there are no restrictions as to the number of such marks. Origin marks 20, 22, 24, 26, and 28 may be in the form of a round dot, but Xs, triangles, squares, circles, and the like may also perform the identical function thereof. Origin mark 20 is shown affixed to surface 18 of adsorbent layer 16 and within channel 32. Origin marks 22, 24, 26, and 28 lie in channels 34, 36, 38, and 40. Plate 10 includes 18 channels which are formed by the removal of a portion of adsorbent layer 16 thereacross. Origin marks 20, 22, 24, 26, and 28 are aligned toward the periphery of adsorbent layer 16. Thus, channels 32, 34, 36, 38, and 40, exemplar of the 18 channels illustrated, run parallel to each other and substantially perpendicular to the aligned origin marks, heretofore described.

Turning to FIG. 1, a plurality of distance marks 42 spaced from the aligned origin marks 22, 24, 26, and 28 and align to measure the progress of liquids in channels 32, 34, 36, 38, and 40. Since the component mixture 30 contains a solvent and a chemical component, it is important to accurately measure the distance travelled by either. Such a system of measurement follows the following formula:

$$R_f = (D_c/D_s)$$

where $D_c$ is the distance travelled by the component, $D_s$ is the distance travelled by the solvent and $R_f$ is the ratio of these two distances. FIG. 1 depicts a developed chromatogram showing the solvent front as having traveled 14 centimeters. Components in channels 32, 34, 36 have formed identifiable spots a lesser distance than solvent front 44. For instance, spot 46 within channel 38, having origin 24 has travelled approximately 10 centimeters. The component responsible for spot 46 would have an $R_f$ value of 0.67. Transparent straight edge 48 easily aligns spot 46 with distance mark 42 denoting 10 centimeters of travel. Other indicia 50 may be placed on surface 18 of adsorbent layer 16 such as serial numbers, company logos, adsorbent layer identification, and the like.

FIG. 3 depicts the common method of applying component 30 to surface 18 of adsorbent layer 16. A micropipette 52 (partially broken) forms a minute drop 54 which would form an origin approximately 3 to 5 millimeters in diameter. In many cases, the component and solvent in mixture 30 will travel along channel 12 without leaving residue. Origin mark 20 permanently fixes the point of contact of drop 54 with surface 18 of adsorbent layer 16.

Markings applied to adsorbent layer 16 are necessarily insoluble in liquid mixture 30. For example, epoxy ink, enamels, and graphite suspended inks may be employed for this purpose. Marking materials 56, FIG. 4, may be applied by silk screening, or rolling a printing plate over the surface 18 of adsorbent layer 16. As shown, a cylinder 58 may have an outer soft flexible printing plate 60 circumjacently disposed thereto. Printing with soft plate 50 does not damage the rather brittle surface 18 of adsorbent layer 16. In addition, the printing plate 60 may be adjusted to produce a "kiss" impression such that surface 18 and plate 60 do not actually touch each other. Marking material 56 transfer takes place by the mere close approach of plate 60 with surface 18.

The invention 10 may be deemed further to include a method of producing a novel thin-layer chromatographic plate by providing a substrate 12 having a supporting surface 14, and depositing an adsorbent layer 16 of material thereupon. Such deposition will provide a surface 18 spaced from substrate 12. Marking material 56 is applied to adsorbent layer 16 to indicate selected position on surface 18 thereof.

Figure 6:
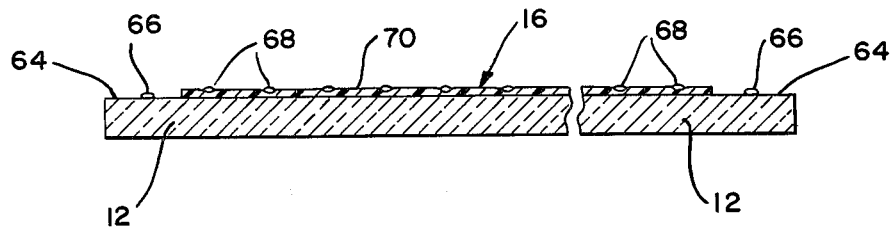
FIG. 6 is a broken view taken along line 6—6 of FIG. 5.

Another embodiment of the invention, FIGS. 5 and 6 may externalize in an adsorbent layer 16 placed on a substrate 12, in the same fashion as heretofore described. However, a portion of the substrate 12, FIG. 6, flanks the outer edge of adsorbent layer 16. The margin 64, which may be integral with substrate 12, at least partially surrounds adsorbent layer 16. A selected marking 66 may be placed on margin 64 to indicate distance of travel of solvent, logos, serial numbers and the like, as heretofore described in prior embodiments of the invention. Likewise, adsorbent layer 16 may take a selective mark 66 on surface 70 to show other desired positions thereon e.g.: origin marks, distance marks and the like.

In operation the user applies a drop 54 of component mixture 30 to origin mark 20. Plate 10, including substrate 12 and adsorbent layer 16 is placed in a solvent bath such that a chromatogram, FIG. 1, develops. In other words, a solvent front 44 moves along channel 32 to the distance mark 42 and identifiable spot 46 forms at a point between origin mark 20 and solvent front 44. The user then measures the distance of travel of spot 46 and the distance of travel of solvent front 44 in relation to origin mark 20. The $R_f$ calculation heretofore described is then easily and conveniently performed.

While in the foregoing specification, embodiments of the invention have been set forth in considerable detail for purposes of making a complete disclosure of the invention, it will be apparent to those of ordinary skill in the art that numerous changes may be made in such detail without departing from the spirit and principals of the invention.

What is claimed is:

1. A prepared thin-layer chromatographic plate for use with liquid matter comprising:
   a. a substrate having a supporting surface:
   b. an adsorbent layer of material deposited on said supporting surface of said substrate said adsorbent layer having a surface spaced from said substrate supporting surface;
   c. marking applied to said adsorbent layer spaced from said substrate supporting surface, said marking comprising an amount of material which does not substantially interact with the liquid matter in the chromatographic process, said marking further comprising at least one origin mark for targeting the spotting of the liquid matter.

2. The thin-layer chromatographic plate of claim 1 in which said marking is printed on said surface of said adsorbent layer spaced from substrate in which said marking material is insoluble in the liquid matter.

3. The thin-layer chromatographic plate of claim 2 in which said at least one origin mark for targeting the spotting of the liquid matter includes a multiplicity of said origin marks, said multiplicity of marks generally aligned away from the center of said spaced surface of said adsorbent layer.

4. The thin layer chromatographic plate of claim 3 which additionally includes a plurality of distance marks aligned and spaced substantially perpendicularly from said aligned origin marks.

5. A prepared thin-layer chromatographic plate for use with liquid matter comprising:
   a. a substrate having a supporting surface;
   b. an adsorbent layer of material deposited on said supporting surface of said substrate, said adsorbent layer having surface spaced from said substrate supporting surface;
   c. a marking applied to said adsorbent layer spaced from said substrate supporting surface, said marking comprising an amount of material which does not substantially interact with the liquid matter in the chromatographic process, said marking including at least one distance mark for monitoring the progress of the liquid matter during the chromatographic process.

6. The thin layer chromatographic plate of claim 5 in which said at least one distance mark includes a plurality of such marks generally aligned away from said at least one origin mark.

7. A method of producing thin layer chromatographic plates for use with liquid matter comprising the steps of
   a. providing a substrate having a supporting surface;
   b. depositing an adsorbent layer of material on said supporting surface of said substrate and providing a surface on said adsorbent layer spaced from said substrate thereby;
   c. applying at least one marking to said adsorbent layer by placing an amount of material which does not substantially interact with the liquid matter on said adsorbent layer to indicate a selected position on said surface of said adsorbent layer spaced from said substrate supporting surface said marking comprising at least one origin mark for targeting the spotting of the liquid matter.

8. The method of claim 7 which additionally includes the step of providing a marking material insoluble in the liquids after said step of applying at least one marking to said adsorbent layer.

9. The method of claim 8 in which said step of applying at least one marking to said adsorbent layer comprises printing said insoluble marking material upon the surface of said adsorbent layer spaced from said substrate.

10. A thin-layer chromatographic plate for use with liquid matter comprising:
    a. a substrate;
    b. an adsorbent layer of material deposited on said substrate, said adsorbent layer presenting a surface adapted for contact with the liquid matter, said substrate supporting said adsorbent layer;
    c. marking selectively applied to said adsorbent layer and said substrate, said marking visible when viewed in relation to said contact of said adsorbent surface with the liquid matter, said marking including at least one origin mark adapted for targeting the spotting of the liquid matter said at least one origin mark being applied to said adsorbent layer.

11. The thin-layer chromatographic plate of claim 10 in which said marking embraces a plurality of markings and includes at least one distance mark spaced from said at least one origin mark.

12. The thin-layer chromatographic plate of claim 11 in which said at least one origin mark is composed of marking material insoluble in the liquids.

13. The thin-layer chromatographic plate of claim 12 in which said at least one origin mark includes a plurality of origin marks aligned on the surface of said adsorbant layer.

14. A method of producing thin-layer chromatographic plates for use with liquid matter comprising the steps of:
    a. providing a substrate having a supporting surface;
    b. depositing an adsorbent layer of material on said supporting surface of said substrate and providing a surface on said adsorbent layer spaced from said substrate thereby;

c. applying at least one marking to said adsorbent layer by placing an amount of material which does not substantially interact with the liquid matter on said adsorbent layer to indicate a selected position on said surface of said adsorbent layer spaced from said substrate supporting surface, said marking comprising at least one distance mark for monitoring the progress of the liquid matter during the chromatographic process.

15. A prepared thin-layer chromatographic plate for use with liquid matter comprising:

a. a substrate
b. an adsorbent layer of material deposited on said substrate, said adsorbent layer presenting a surface adapted for contact with the liquid matter, said substrate supporting said adsorbent layer;
c. a marking applied to said adsorbent layer spaced from said substrate supporting surface, said marking comprising an amount of material which does not substantially interact with the liquid matter in the chromatographic process, said marking including at least one identification mark for distinguishing the thin-layer chromatographic plate.